United States Patent [19]
Santti et al.

[11] Patent Number: 5,972,921
[45] Date of Patent: Oct. 26, 1999

[54] USE OF AN AROMATASE INHIBITOR IN THE TREATMENT OF DECREASED ANDROGEN TO ESTROGEN RATIO AND DETRUSOR URETHRAL SPHINCTER DYSSYNERGIA IN MEN

[75] Inventors: Risto Santti, Naantali; Antti Talo, Littoinen; Tomi Streng, Turku; Kaija Halonen, Rusko; Lauri Kangas, Raisio; Risto Lammintausta, Turku, all of Finland

[73] Assignee: Hormos Medical Oy Ltd., Turku, Finland

[21] Appl. No.: 08/989,447

[22] Filed: Dec. 12, 1997

[51] Int. Cl.⁶ .......................... A61K 31/56; A61K 31/44; A61K 31/445; A61K 31/41
[52] U.S. Cl. .......................... 514/177; 514/179; 514/300; 514/318; 514/383
[58] Field of Search .................................. 514/383, 300, 514/318, 177, 179

[56] References Cited

FOREIGN PATENT DOCUMENTS

WO 94/13645  6/1994  WIPO .

OTHER PUBLICATIONS

Allan R. Glass, MD, "Gynecomastia,"23 *Clinical Andrology* 825–837 (Dec. 1994).
Bruno de Lignieres, "Transdermal Dihydrotestosterone Treatment of Andropause,"25 *Ann Med* 235–241 (1993).
Albert Radlmaier et al., "Estrogen Reduction by Aromatase Inhibition for Benign Prostatic Hyperplasia,"29 *The Prostate* 199–209 (1996).
Joseph E. Osterling et al., "Aromatase Inhibition in the Dog,"139 *The Journal of Urology* 832–839 (Apr. 1988).
Heinz Schilcher, "Miktionsbeeinflussende Mittel zur Behandlung der BPH, " *Phytotherapie in der Urologie* 69–93 (1992).

*Primary Examiner*—William R. A. Jarvis
*Attorney, Agent, or Firm*—Adduci, Mastriani & Schaumberg, L.L.P.

[57] ABSTRACT

The invention relates to a method for the treatment of detrusor urethral sphincter dyssynergia in men, said method comprising administering to the patient an effective amount of an aromatase inhibitor. The invention also concerns a method for the treatment of decreased androgen to estrogen ratio in men, said method comprising administering to the patient an effective amount of an aromatase inhibitor.

8 Claims, 8 Drawing Sheets

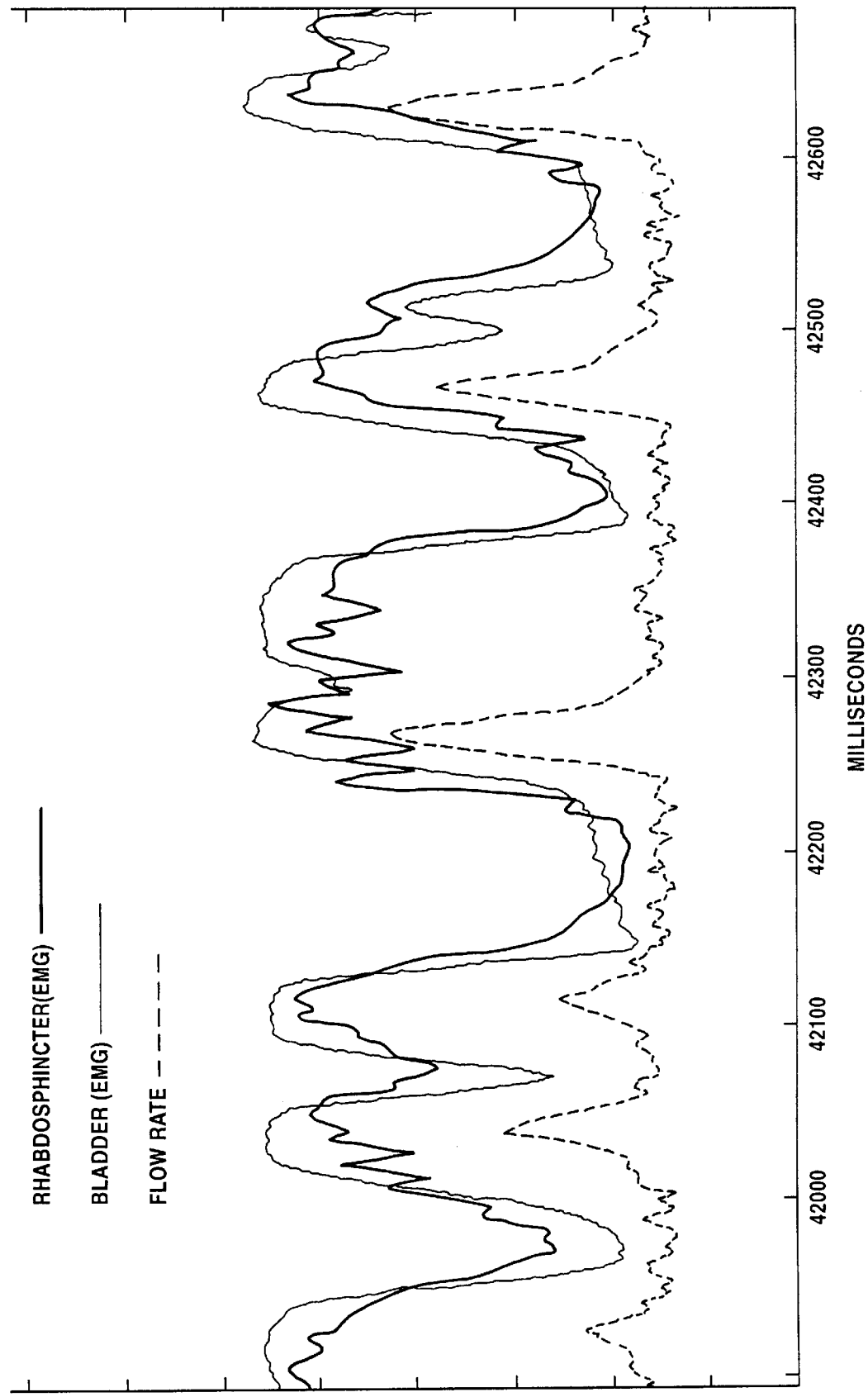

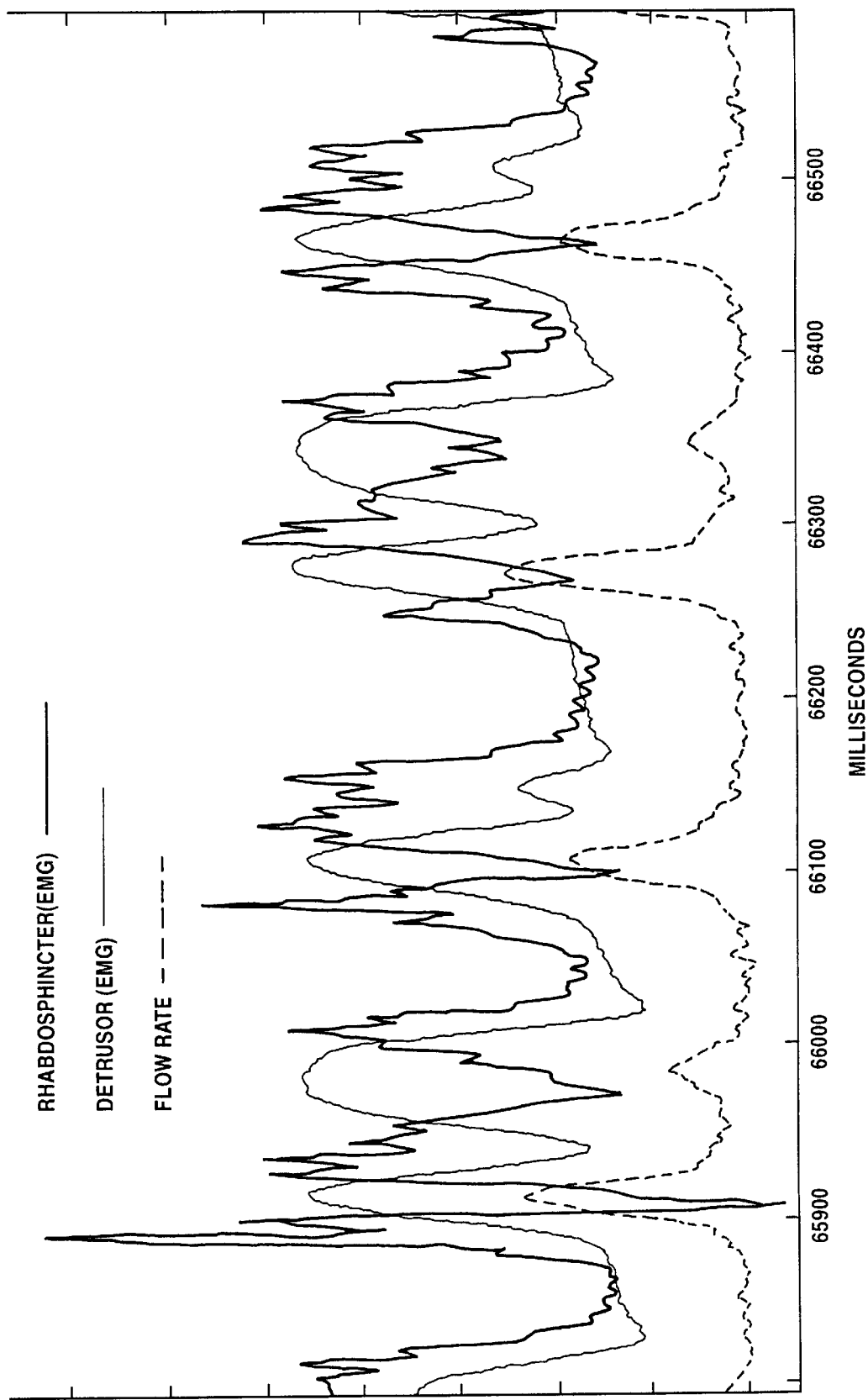

USE OF AN AROMATASE INHIBITOR IN THE TREATMENT OF DECREASED ANDROGEN TO ESTROGEN RATIO AND DETRUSOR URETHRAL SPHINCTER DYSSYNERGIA IN MEN

This invention relates to a method for the treatment of decreased androgen to estrogen ratio (DATER) as well as to a method for the treatment of detrusor urethral sphincter dyssynergia (DUSD) in men. Furthermore, the invention concerns a method for the in vivo investigation of the influence of a certain condition on the urinary function of male individuals using an animal model of male rodents.

BACKGROUND OF THE INVENTION

The publications and other materials used herein to illuminate the background of the invention, and in particular, cases to provide additional details respecting the practice, are incorporated by reference.

Detrusor urethral sphincter dyssynergia (DUSD) and its current therapies

Normal voiding consists of sustained relaxation of peri-urethral smooth and striated muscle during sustained detrusor contraction. The anatomy of the lower urinary tract in human (a) and in rat (b) is shown in FIG. 2. In this Figure D denote detrusor, U urethra, RB rhabdosphincter (striated urethral sphincter), PR prostate, VPR ventral prostate, LPR lateral prostate, S seminal vesicle, C coagulating gland and UR urogenital diaphragm. Inappropriate contraction or failure of complete and sustained relaxation of the urethral musculature during detrusor contraction causes voiding problems known as detrusor urethral sphincter dyssynergia. The etiopathogenesis of detrusor urethral sphincter dyssynergia is poorly understood. Three different clinical outcomes have been described: 1) bladder neck dyssynergia, 2) external sphincter pseudodyssynergia and 3) Hinman syndrome. They all are defined in this invention as detrusor urethral sphincter dyssynergia.

In the following we summarize the clinical symptoms of male functional detrusor urethral sphincter dyssynergia and its treatments taking into account especially the possible hormonal background of the symptoms.

According to the recent study (Kaplan et al. 1996) half of the men younger than 50 years old with chronic irritative and/or obstructive voiding symptoms have primary bladder outlet obstruction (bladder neck dyssynergia), and in every fourth patient, the obstruction is located to the membraneous urethra (termed as pseudodyssynergia of the external sphincter).

Bladder neck dyssynergia

The bladder neck dyssynergia patient is a male aged between 20 and 60 years. Bladder neck dyssynergia is usually a life-long condition. It virtually never occurs in females. At old ages, prostatic enlargement and bladder neck dyssynergia are both common conditions so their coincidence is by no means uncommon.

Symptoms of bladder neck dyssynergia are hesitance, poor urinary stream, terminal drippling and incomplete bladder emptying (Prostatic Obstruction. Pathogenesis and treatment. Ed. Christopher R. Chapple. Springer-Verlag 1994). In bladder neck dyssynergia an increased intraluminal bladder pressure in needed to empty the bladder. In the initial stages, there is no reduction in the flow rate because the maximum micturition pressure compensates for the increased outflow resistance. Patients with bladder neck dyssynergia may develop secondary detrusor instability with irritative symptoms of frequency, urgency and nocturia.

In bladder neck dyssynergia, the proximal urethra actively tightens during voiding. Smooth muscle fibers of the proximal part of the male bladder neck are morphological extensions of the cholinergically innervated detrusor fibers. The smooth muscle fibres of the distal part of the male bladder neck are morphologically distinct from the detrusor fibres and have α-adrenergic innervation. It is possible that dysfunctional bladder neck has abnormal composition or arrangements of the smooth muscle fibers. Alterations in the contractile properties or responses of smooth muscle cannot be excluded, either. There is little evidence to support the role of smooth muscle cell hyperplasia or hypertrophy in the development of the dysfunction in men.

Bladder neck dyssynergia can be treated surgically by transecting the full thickness of the bladder neck musculature. The selective α1-adrenoceptor antagonists, such as prazosin and indoramin inhibit symphatetic tone which is supposed to exacerbate the degree of obstruction of urethra through contraction of urethral smooth muscle. They used as an adjunct in the symptomatic treatment of functional urethral obstruction. Uroselective α1-antagonists with high tissue selectivity for lower urinary tract smooth muscle that do not provoke hypotensive side-effects are under development.

External sphincter pseudodyssynergia

Increased voiding pressure or decreased flow rate are not necessarily only associated with structural or functional changes in the smooth muscle component of the lower urinary tract. Distally the prostatic urethra possesses a smooth muscle merging with the prostatic musculature. Caudal to the prostate, the urethral wall has a striated muscle layer called rhabdosphincter, urethral sphincter or external sphincter. The striated muscle extends throughout the length of the pre-penile urethra (Oelrich 1980). The proximal portion of the sphincter lies as a bundle between the base of the bladder and the proximal border of the prostate. The fibers in the central portion of the sphincter cover the lateral surface of the prostate. Caudal to the prostate, striated muscle form a horse-shoe -shaped configuration (Strasse et al. 1996). Inferior to the pelvic diaphragm, the sphincter (external sphincter) expands to fill the area between the pudendal canals (Oelrich 1980). There is no subdivision of the human urethra sphincter muscle, and no smooth muscle septa have been recognized dividing the muscle.

During the normal micturition cycle, an increase in external sphincter electromyographic activity accompanies bladder filling (continence reflex). This is followed by relaxation of the urethral sphincter and the pelvic floor muscles, which begins before or at the beginning of the detrusor contration and persists throughout the contration. External sphincter dyssynergia is defined as an inappropriate increase in striated urethral muscle (external urethral sphincter) activity during a detrusor contraction and is a well recognized cause of voiding dysfunction in patients with upper neurone lesions. This overcompensation is done to counteract the elevated bladder pressure caused by uninhibited detrusor contraction (an exaggerated continence reflex) (Rudy et al. 1988).

Most striking in all of the patients with pseudodyssynergia is the presence of contraction of the striated urethral/external sphincter during voiding (Kaplan et al. 1997). In adults, the etiology of the sphincter pseudodyssynergia may be less neurological and more functional which can be seen as narrowing of or cutting off the urinary stream during micturition (Kaplan et al. 1997). Men who have pelvic floor spasm or what Kaplan et al. (1996) term as pseudodyssynergia, may not have severely elevated voiding pressures. However, they have narrowing of the urinary stream during voiding at the level of the membraneous urethra.

Hinman syndrome

Urodynamic investigations in children with an abnormal voiding pattern have shown dyssynergia between the detrusor and striated urethral sphincter in the absence of neurologic disease (nonneurogenic neurogenic bladder or the Hinman syndrome) (Hinman and Baumann, 1973). This appears to result from unintentional, habitual contractions of the striated urethral sphincter in response to involuntary bladder contraction to prevent urinary incontinence. This dyssynergia probably may at least partly represent a learned habit. Its more common among girls than boys. Pharmacologic manipulation of detrusor and sphincter function and biofeedback therapy have been highly successful. The relationship between the Hinman syndrome and the detrusor sphincter dyssynergia or urethral sphincter pseudodyssynergia is not known.

We suggest that the development of detrusor urethral sphincter dyssynergia is associated to estrogen or androgen/ estrogen ratio. To the best of our knowledge, the hormonal etiology for the male detrusor urethral sphincter dyssynergia has not been considered earlier.

Decreased androgen to estrogen ratio (DATER)

Elderly women are known to experience commonly postmenopausal syndromes during and after the menopause. In men the hormonal changes are not as dramatic as in women, but recently more attention has been paid to andropause. There are at least three groups of men who are exposed to excessive amounts of estrogens and have relative androgen deficiency. One group includes sons of mothers who have been given diethylstilbesterol (DES) to prevent threatening abortion and gynecomastic boys whose fat tissue is an extra source of estrogens and who may be exposed to estrogen throughout their life, or overweighed elderly men whose low physical activity allows accumulation of fat tissue producing high amounts of estrogens. Another group consists of elderly men who have been exposed to environmental estrogens and men on high fat and low fibre diets. A relative androgen deficiency is a common phenomenon in obese elderly men. The prevalence of androgen deficiency is about 20% in men aged 60 to 80 yrs and 35% in men over 80 yrs. In contrast to severe symptoms in women, the andropause develops slowly and easily remains unrecognized.

In theory, DATER can be treated by testosterone. However, testosterone is converted in the body by aromatase enzyme to estrogens. The long term effect may actually be decreased production of endogenous androgens and concomitantly increased androgen to estrogen ratio. Therefore high doses of testosterone may cause hypogonadism and endocrinological effects which resemble estrogenization. There is no clinically established medicine for the treatment of DATER.

Possible role of estrogens in the development of detrusor urethral sphincter dyssynergia; Estrogen receptors and actions in the lower urinary tract of the experimental animals and men Although there is no direct evidence to support the role of estrogens in the development of the detrusor urethral sphincter dyssynergia in man there are data to support this: 1. estrogens increase both the density of adrenergic receptors and the adrenergically mediated contractile responses of urethral smooth muscle; and 2. estrogens alter, by preventing androgen-induced sex differentiation or by maintaining of estrogen-dependent structures, the innervation of striated urethral sphincter and the pelvic floor muscles; both of these two estrogen actions could alter the function of the lower urinary tract, and account for the detrusor urethral sphincter dyssynergia.

As a sign of estrogen responsiveness, human bladder and urethra have shown to contain stromal estrogen receptors (ER). The concentrations of estrogen receptors in the trigonum and bladder are considerably lower than those in the urethra (Iosif et al. 1981). Further, the concentrations are higher in the middle and distal thirds of the female intrapelvic urethra in comparison to proximal urethra (Wilson et al. 1984). This suggests that the middle and distal urethra are the most estrogen-sensitive parts in the female lower urinary tract. The female pelvic floor muscles and ligaments also possess estrogen receptors (Smith et al. 1990).

It is known that estrogen can influence the response of urethra to alfa adrenergic stimulation. $\alpha$-adrenoceptors play a significant role in the maintenance of intraurethral pressure. In the sexually mature male, the $\alpha$-adrenoceptors in urethra are mainly of the $\alpha 1$-subtype. $\alpha 1$-adrenoceptors are unevenly distributed along the male urethra (Yablonsky et al. 1991). The highest densities of $^3$H-prazosin binding sites have been found in the preprostatic urethra of the dog. The binding sites were localized on the smooth muscle fibers. Urethral striated muscle had no $\alpha 1$-adrenoceptors.

In the female urethra, $\alpha 2$- adrenoceptors predominate. The sex difference in the densities of $\alpha 1$- and $\alpha 2$-receptors between the male and female urethra may be due to estrogen. In the female rabbit urethra, the estrogen-induced increased sensitivity to norephinephrine is attributable to an increase in the number of postjuntional $\alpha 2$-adrenoceptors (Larsson et al. 1984). Further, castration of the male rabbit increased $\alpha 2$-receptor density slightly but it was increased markedly after estrogen administration (Morita et al. 1992). $\alpha 1$-adrenergic receptor densities decreased significantly after castration, and were not affected by estrogen administration. As a conclusion, estrogen may decrease the ratio of $\alpha 1$- to $\alpha 2$-receptors in the smooth muscle of the male urethra, and by this change alters the sympathetic control of urethral contraction.

The second possibility for estrogen interference with the control of the male voiding lies in the innervation of urethral striated muscle. There are sexually dimorphic nuclei in the spinal cord. The volumes of the nuclei of the male rat are larger than those of the female. It is known that higher levels of androgens in male rats prevent SNB (the spinal nucleus of the bulbocavernosus) and DLN (the dorsolateral nucleus) motoneurons from dying during early developoment. The levator ani is among the targets of SNB. The DLN has two targets: the ischiocavernosus, and the striated urethral sphincter. Androgens can also prevent synapse elimination in the sexual dimorphic levator ani muscle and alter the pattern of innervation that is seen in adulthood. The hormone-induced loss of neurones and synapses could simulate the well recognized cause of the inappropriate increase in sphincteric activity during a detrusor contraction seen in patients with upper neurone lesions.

Besides growth inhibition, long-term administration of estrogen or aromatizable androgen to intact or castrated adult males of various animal species promotes prostatic growth at distinct periurethral sites. These sites responding to estrogen treatment with induction of epithelial metaplasia, hyperplasia or dysplasia have been found to occur in the prostate of several animal species (monkeys, dogs, guinea pigs, rats and mice). The location of nuclear estrogen receptors (ERs) found in the stroma corresponds to the sites of histological changes demonstrated in the monkey, dog and mouse. ERs have also been found in the periurethral region of the human prostate, suggesting a homology of the posterior periurethral region of the prostate (containing the collecting ducts and periurethral glands) across the species. To our knowledge, none of the models of estrogen-related altered prostatic growth have been characterized urodynamically, and thus the pathophysiological significance of estrogen-related altered periurethral prostatic growth for voiding remains unclear. As signs of possible urethral obstruction, enlarged bladder, thickened bladder wall and bladder stones have occasionally been seen in estrogen-treated animals. Although higher than physiological blood levels of the female hormone are required for promotion of periurethral prostatic growth in adult animals, its occurrence suggests that estrogen or the decreased androgen to estrogen ratio may be involved in the normal and hyperplastic growth of the human prostate as well as in the development of detrusor urethral sphincter dyssynergia.

SUMMARY OF THE INVENTION

According to one aspect, the invention concerns a method for the treatment of detrusor urethral sphincter dyssynergia in men, said method comprising administering to the patient an effective amount of an aromatase inhibitor.

According to another aspect, the invention concerns a method for the treatment of decreased androgen to estrogen ratio in men, said method comprising administering to the patient an effective amount of an aromatase inhibitor.

According to a third aspect, the invention relates to a method for the in vivo investigation of the influence of a certain condition on the urinary function of male individuals using an animal model of male rodents wherein said rodents have been
- subjected to said condition,
- anesthetized,
- provided with a pressure transducer connected to an infusion cannula inserted in the bladder, a flow probe inserted in the distal urethra and connected to a flow meter,
- infused with a solution into the bladder to induce micturition, and wherein the bladder pressure and urinary flow are registered as function of time. The method is characterized in that said rodents have also been provided with electrodes attached to muscles of the lower urinary tract, and that the electrical activity of said muscles are registered simultaneously with the registering of the bladder pressure and the urinary flow.

BRIEF DESCRIPTION OF THE DRAWINGS

FIG. 6 shows the electrical activity of the rhabdosphincter (EMG), bladder (detrusor) (EMG) and flow rate versus time in a neoDES rat, and FIG. 7 shows the electrical activity of the rhabdosphincter (EMG), bladder (detrusor) (EMG) and urine flow rate versus time in a neoDES rat that have been treated with the aromatase inhibitor MPV-2213ad for 6 weeks.

DETAILED DESCRIPTION OF THE INVENTION

This invention relates to the use of aromatase inhibitors in men for the treatment of detrusor urethral sphincter dyssynergia causing obstructive voiding dysfunction. The principal cause of this dysfunction may include early estrogenization (demasculinization) and/or excessive estrogen production and subsequently decreased androgen to estrogen ratio (DATER) in the male organism in serum and/or steroid hormone target tissues. In these cases enlargement of the prostate may or may not be present.

Figure 1:
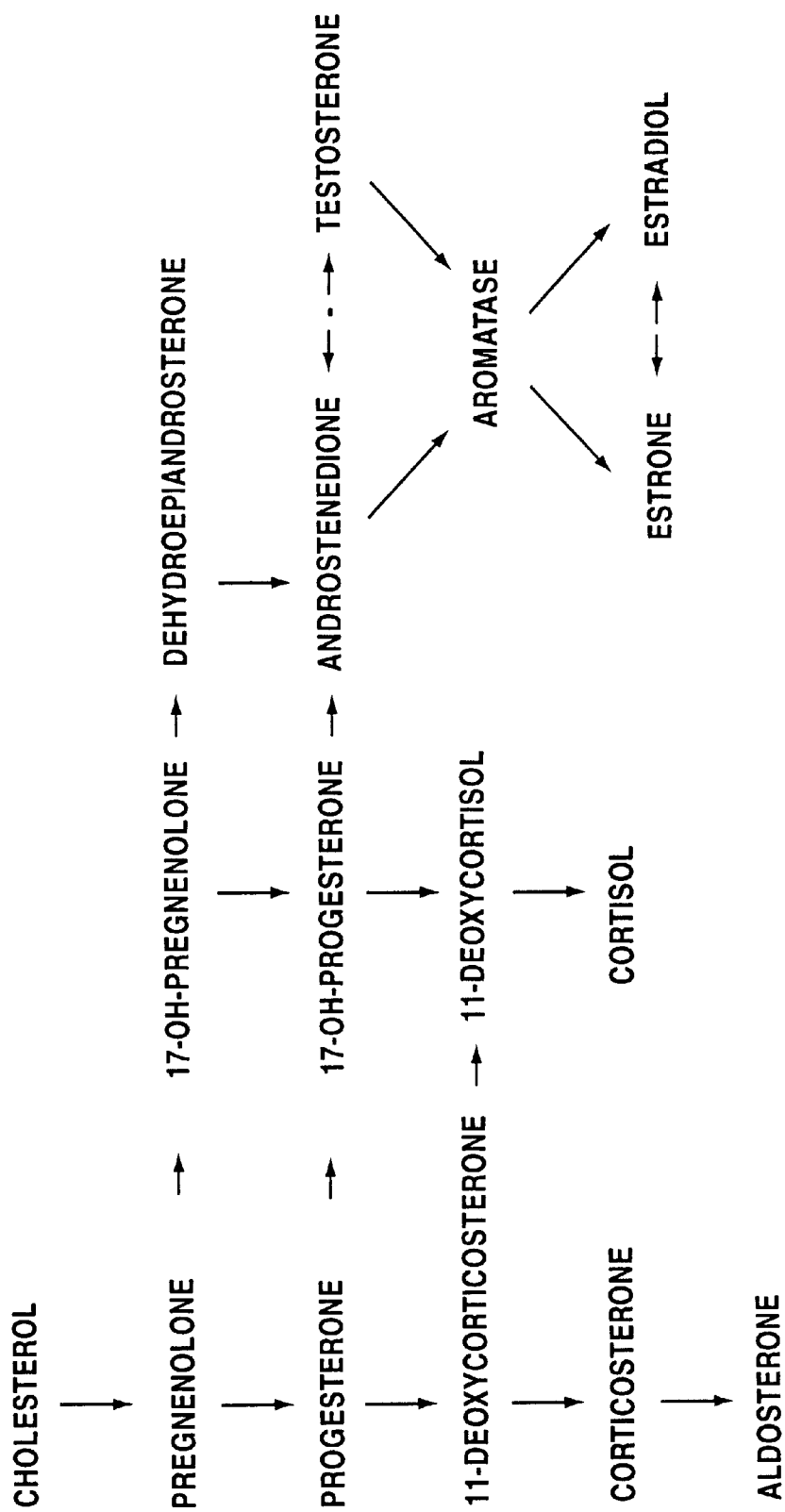
FIG. 1 shows the metabolism of of steroids with a special reference to aromatase and its inhibition.
Figure 2B:
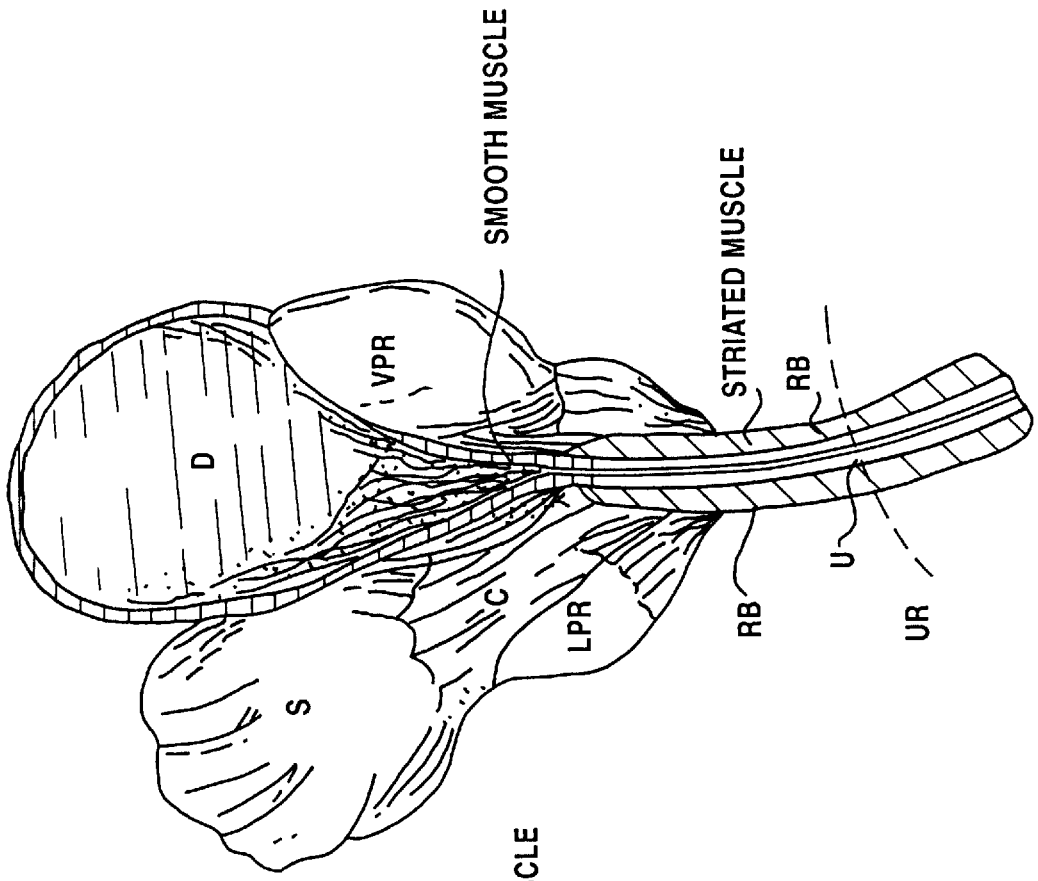
FIG. 2 shows the human resp. rat male lower urinary tract.
Figure 2A:
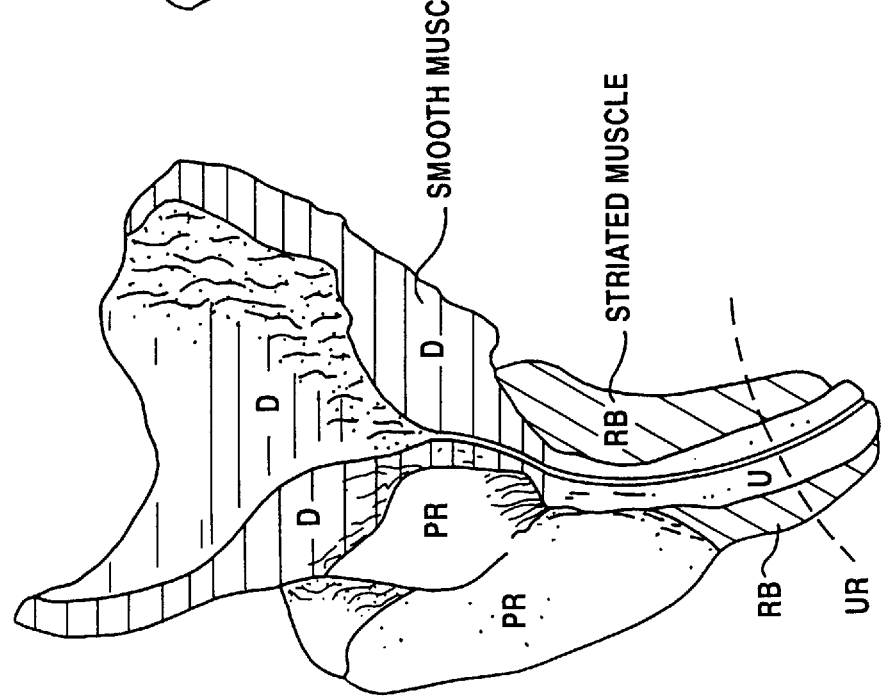

This invention also relates to the use of aromatase inhibitors in the treatment of decreased androgen to estrogen ration in men, for example male climacterium or andropause which is due to the relative androgen deficiency in men. These symptoms of andropause may include benign prostatic hypertrophy (BPH), erectile dysfunction, impotence, infertility, gynecomastia (especially juvenile gynecomastia), decreased muscle mass, obesity, bone mass and fitness, and subsequent psychological symptoms. In this invention we propose that it is possible to improve the DATER by aromatase inhibitors. These drugs effectively and specifically increase the androgen to estrogen ratio. They may be given safely to men to treat all syndromes and symptoms which are due to relative androgen deficiency (DATER). These drugs inhibit the conversion of androgens to strogens and thus benefit the subject in two ways, by decreasing estrogen levels and increasing androgen levels (FIG. 1).

Aromatase is an enzyme complex involving a NADPH-cytochrome C reductase and a specific cytochrome P-450 protein. The reaction which is catalyzed by aromatase is unique in the biosynthesis of steroids, as it involves conversion of ring A of the steroid structure to an aromatic ring with the loss of the angular C-19 methyl group and cis-elimination of the 1β and 2β hydrogens to yield estrogen and formic acid. Aromatization is the last and critical step in the biosynthesis of estrogens from cholesterol (see FIG. 1). Therefore, specific blockade of this enzyme does not cause deprivation of other essential steroids such as cortisol or male sex hormones.

As suitable selective aromatase inhibitors can be mentioned, for example, the compounds coverd by formula (I) in International patent application publication No. WO 94/13645. Said compounds

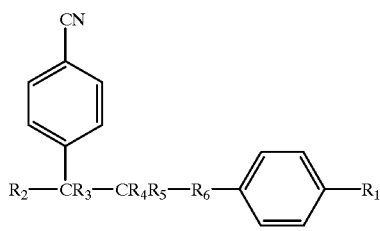

(I)

include members wherein $R_1$ is hydrogen, methyl, methoxy, nitro, amino, cyano, trifluoromethyl, difluoromethyl, monofluoromethyl or halogen; $R_2$ is a heterocyclic radical selected from 1-imidazolyl, triazolyl, tetrazolyl, pyrazolyl, pyrimidinyl, oxazolyl, thiazolyl, isoxazolyl and isothiazolyl; $R_3$ is hydrogen or hydroxy; $R_4$ is hydrogen; $R_5$ is hydrogen or hydroxy; or $R_4$ is hydrogen and $R_3$ and $R_5$ combined form a bond; or $R_3$ is hydrogen and $R_4$ and $R_5$ combined form =O; $R_6$ is methylene, ethylene, —CHOH— , —CH$_2$CHOH— , —CHOH—CH$_2$— , —CH=CH— or —C(=O)— ; or $R_4$ is hydrogen and $R_3$ and $R_6$ combined is =CH— or =CH—CH$_2$— ; or a stereoisomer, or a non-toxic pharmaceutically acceptable acid addition salt thereof.

A preferred compound of this group 1-[1-(4-cyanophenyl)-3-(4-fluorophenyl) -2-hydroxypropyl]-1,2,4-triazole. Particularly preferred is the compound 1-[1-(4-cyanophenyl) -3-(4-fluorophenyl)-2-hydroxypropyl]-1,2,4-triazole, diasteroisomer a+d, which also is known under the code MPV-2213ad.

As examples of other suitable aromatase inhibitors can be mentioned anastrozole, fadrozole, letrozole, vorozole, roglethimide, atamestane, exemestane, formestane, YM-511 (4-[N-(4-bromobenzyl)-N-(4-cyanophenyl)amino]-4H-1,2,4-triazole), ZD-1033 (arimedex) and NKS-01 (14-α-hydroxyandrost-4-ene-3,6,17-trione) and their stereoisomers and non-toxic pharmaceutically acceptable acid addition salts.

MPV-2213ad, like all presently described specific aromatase inhibitors, have been intended mainly for the treatment of female breast cancer where estrogens stimulate the tumor growth, and aromatase inhibitor, by depleting estrogens, inhibits the tumor growth. In men aromatase inhibitors dramatically decrease estradiol concentrations and may simultaneously increase the testosterone concentrations being thus especially beneficial for the increasing the DATER and for the treatment of voiding dysfunction which are due to the DATER, as described in this invention.

For the purpose of this invention, the aromatase inhibitor or its stereoisomer or pharmaceutically acceptable salt can be administered by various routes. The suitable administration forms include, for example, oral formulations; parenteral injections including intravenous, intramuscular, intradermal and subcutanous injections; and transdermal or rectal formulations. Suitable oral formulations include e.g. conventional or slow-release tablets and gelatine capsules.

The required dosage of the aromatase inhibitors compounds will vary with the particular condition being treated, the severity of the condition, the duration of the treatment, the administration route and the specific compound being employed. For example, MPV-2213ad can be administered perorally preferentially once daily. The daily dose is 1–30 mg, preferably 3–10 mg. MPV-2213ad can be given as tablets or other formulations like gelatine capsules alone or mixed in any clinically acceptable non-active ingredients which are used in the pharmaceutical industry.

This invention also relates further to a new methodology which enables studying the urodynamics in rats, when applied accordingly, in such detail that has not been possible earlier. The method according to the invention is based on combining urinary flow and bladder pressure with simultaneous measurements of the electrical activity on the smooth muscles of the lower urinary tract (e.g. detrusor, bladder neck and rhabdosphincter).

The signals from the registered bladder pressure, urinary flow, and electrical activity of the detrusor, bladder neck and rhabdosphincter muscles are transferred to a programmed computer and optionally also displayed.

The rodents, e.g. rats can for example be administered with an agent, the influence of which on the urinary function of said rodent shall be investigated. The animal model can also be used to study the influence of certain physical conditions on the rodents' urinary function.

According to a preferred application, the method is used to investigate the ability of a certain compound to reverse a condition of detrusor urethral sphincter dyssynergia that has been induced in the rodent. After the induced dyssynergia, the rodents have been administered with an agent which shall be investigated in respect of its effect in the treatment of detrusor urethral sphincter dyssynergia.

This model allows urodynamic studies in combination with morphological investigations, because, contrary to previous methods, the new method which registers the action potential of smooth muscles and striated sphincter muscles in the lower urinary tract gives information on the location of areas that should be subjected to morphological investigations.

Initiated by accidental findings, the studies of the voiding problems of neonatally estrogenized rats were systematically continued. The increase in the maximum pressure during rapid oscillation and decreased flow rate indicate incomplete opening of the bladder neck and/or urethral lumen at a time when the detrusor muscle is contracted and voiding initiated. No marked increase was seen in the periurethral glandular mass, and thus it is unlikely that periurethral glandular tissues cause static occlusion of the urethral lumen.

This animal model allows the reproduction of the urodynamics (increased bladder pressure, decreased flow rate, intermittency and prolongation of the micturition time) characteristics for men with incomplete opening disorder of the detrusor/urethral dyssynergia. Although the animal model cannot be directly extrapolated to humans, it is now for the first time possible to analyse quantitatively and simultaneously the physiological processes in normal and altered voiding without mechanical obstruction. Similar measurements can be used in the future also in humans for differential diagnosis of urethral dysfunctions.

The animal model for the detrusor urethral sphincter dyssynergia is constructed in the following way. Male Noble rats were treated neonatally with estrogen (10 μg of diethylstilbestrol (DES) daily s.c. on days 1–5 of postnatal life). After the treatment with diethylstilbestrol, the rats were left to develop normally without any treatments for 5–6 months in standardized conditions. The dysfunction of the detrusor and urethra develops during this time.

The measurements of the electrical activity of the muscles of the lower urinary tract showed that neonatal exposure to estrogen (diethylstilbestrol, DES) predisposes the male rat to urethral opening disorder which is due to detrusor urethral sphincter dyssynergia. Increased maximum voiding pressure in the bladder is not necessarily only associated with structural changes in the smooth muscle component of the urethral wall. Smooth muscle cells are surrounded by the rhabdosphincter in the middle and distal parts of the urethral wall in the rat (from the level of urethral inlets of ejaculatory ducts and prostatic collecting ducts under the interior surface of the pelvic floor).

It is not yet understood how estrogens can change muscular structure and function. Estrogens could influence smooth muscle activity through effects mediated by the autonomic nervous system. It has been suggested that the density of $\alpha_2$-adrenergic receptors and contractile responses of urethral smooth muscle cells to neurotransmitters is increased by estrogens in male and female rabbits. However, no evidence is available for a direct estrogen effect on urethral smooth muscle cells and, consequently, on the urodynamic parameters of men or women. Early estrogenization could alter the relative contribution of different embryonic tissues (e.g. including the Müllerian ducts) to the formation of urethral muscle tissue.

We describe our experience of using the developed method in investigating the effect of neoDES-treatment on the urinary function and reversal of the urinary dysfunction by the aromatase inhibitor MPV-2213ad. The 5-month old control and neonatally estrogenized rats were treated with the aromatase inhibitor MPV-2213ad suspended in a vehicle. Carboxyl methyl cellulose (CMC) water solution was used for placebo treatment. For aromatase-inhibitor treatment, 10 mg/kg of MPV-2213 ad was compared with placebo. The treatments were made p.o. for four or six weeks. In this report we use the results mainly of six week study. Our results show that the treatment with aromatase inhibitor reversed the urodynamic changes: the bladder pressure was decreased and the flow rate increased. The codes for different groups are as follows: P stands for placebo, A for aromatase-inhibitor treatment, C for control and D for neonatally estrogenized (neoDES) rats, and n denotes the number of rats.

The method for urodynamical measurements

The novel method for recording the urodynamics of the rat is a combination of transvesical cystometry (Maggi & al., 1986a) with recordings of the flow rate with a flowmeter (van Asselt et. al. 1995) and the electrical activity of the smooth muscles with suction electrodes (Hoffman et. al. 1959). The combination of these previous methods has never been applied to study of rodent urodynamics.

Figure 3:
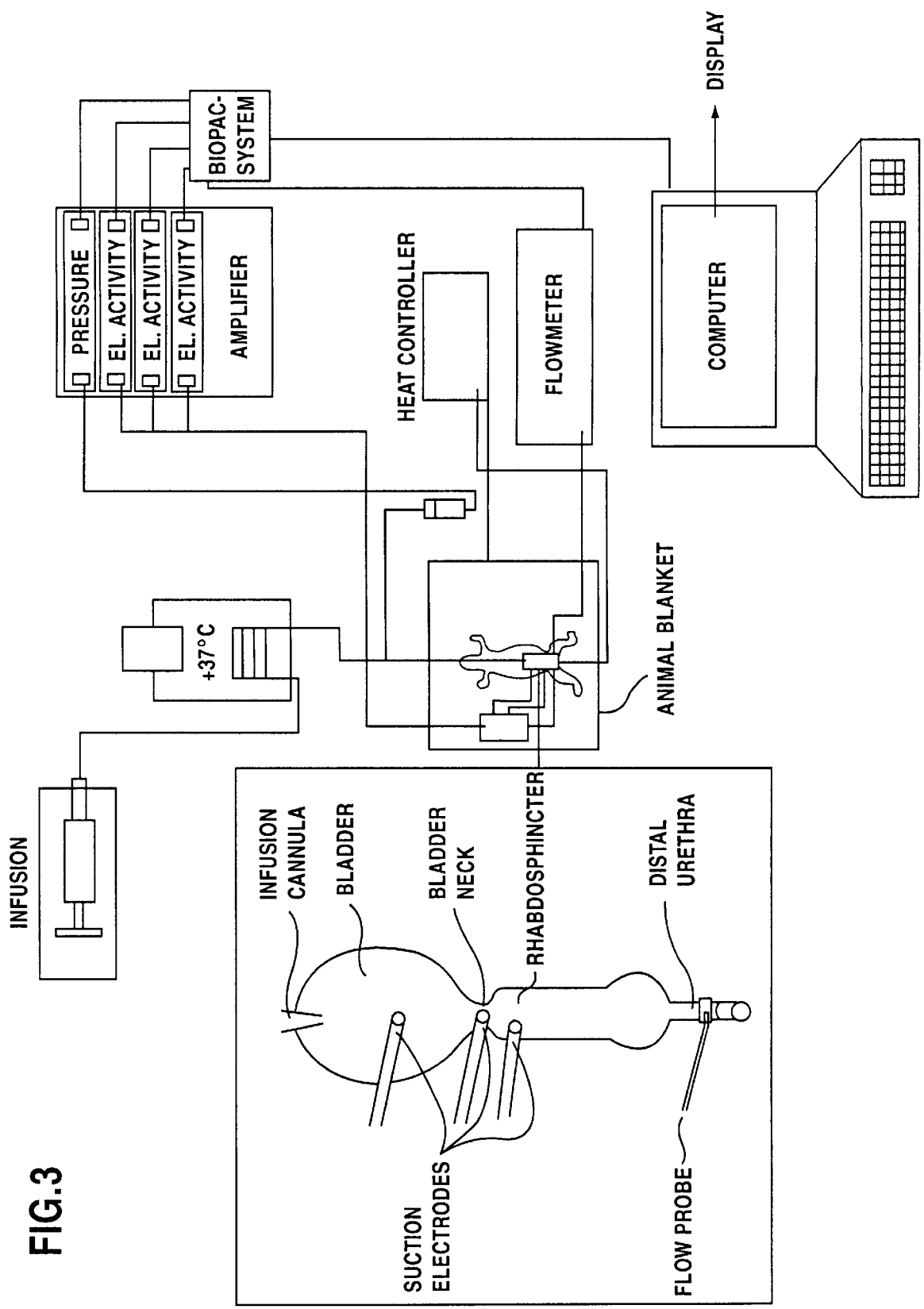
FIG. 3 is a schematic presentation of the method for urodynamical measurements in male rat.

The setup of the method is disclosed in FIG. 3, where an anesthetized rat is used. An infusion cannula is inserted in the bladder. The infusion cannula is connected to an infusion pump and to a pressure transducer. A flow probe is inserted in the distal urethra and connected to a flow meter. The smooth muscles and striated muscle of rhabdosphincter of the rat's urinary tract rat are also provided with electrodes for registering of the electrical activity (EMG) of said muscles. At a certain point of time a solution is infused into the bladder to induce micturition. The bladder pressure, urinary flow and the electrical activities of the muscles are registered as function of time. The setup further includes necessary electronic components such as signal amplifiers and converters, and a programmed computer.

In the specific tests carried out and described below the setup included the following components:
-Amplifier: Grass, Model 7P1122B, Grass Instruments Co., USA
-Pressure transducer: Statham P23BC, Grass Instruments Co., USA
-Suction electrodes: the suction electrodes were made of flexible thinwall silicon tubing (i.d. 1.10 mm and o.d. 2 mm) in which were inserted a thin (0.125 mm) chlorided silver wire (World Precision Instruments, Inc. Sarasota).
-Flowmeter: Transsonic Systems Inc. Animal Research Flowmeter type. T206
-Flow probe: Transonic Systems, Inc. Probe # 2,5SB178
-Infusion pumps: Mikroperpex® peristaltic infusion pump, LKB or B.Braun-Melsungen AG, type 1831, D-3508 Melsungen/West Germany
-Water bath heater: B.Braun, Thermomix® MM, type 852102/6, Melsungen/West Germany
-Animal heating blanket: Harvard Animal Blanket control unit (type 50-7061, Harvard Apparatus Limited, Edgenbridge, England)
-Signal converter: Biopac-system MP 100 A, Biopac Systems Inc., Santa Barbara, Calif.
-Recording program: Acq Knowledge 3.02 (MP100 Manager Version 3.02, Copyright© 1992–95 BIOPAC Systems Inc.).

Experiments

The rats were anesthetized with chloral hydrate (0.9 g/kg; Sigma Chemical Co. St. Luis. Mo. 63178, U.S.A.) i.p. The anesthesia was maintaind with urethane (0.32 g/kg; Sigma Chemical Co. St. Luis. Mo. 63178, U.S.A.) i.v. if needed. The body temperature was kept constant at +36–38° C. by a thermostatically controlled animal blanket and if needed, with a heating lamp. The bladder and the distal part of urethra were exposed with a midline incision of the lower abdomen. In transvesical cystometry a 20G i.v. cannula was inserted through the bladder apex into the lumen. The cannula was connected to an infusion pump and to a pressure transducer. The whole system was filled with saline. Measurements were made at the infusion rate of 0.185 ml/min. An ultrasonic flow probe was used for measurement of the flow rate from the distal part of urethra. The flow probe was connected to a flow meter. With sampling rate of 100 Hz. At the same time with the measurements of transvesical cystometry and flow rate, the electrical activity of the detrusor, bladder neck and striated urethral sphincter (rhabdosphincter) were measured extracellulary with suction electrodes. The electrodes were attached onto ventral surface of the muscles by suction (provided by a flow of tap water). The suction electrodes and pressure transducer were connected to an amplifier. In electrical activity measurements we used 0.8 Hz low frequency AC coupling. The reference and ground electrodes were placed on the side of the wound so that EKG signal was not observable. The tissues were kept moist during measurements with warm (+37° C.) saline. The pressure and voltage signals were transferred to the Biopac-system as well as the flow meter signals. The Biopac-system was connected to a personal computer. Continuous recording was made with Acq Knowledge 3.02 program with sample rate of 400 Hz. The analysis of data was carried out with the same program. Three representative voidings were chosen for further analysis. Statistical analysis was carried out with ANOVA. The tables shows the significations in p-values (post-hoc ;LSD -test).

Results

Effects of aromatase inhibitor (MPV-2213ad) on voiding functions of the control and neonatally estrogenized male rats In this study we compared the recordings between placebo- and aromatase-inhibitor treated control and neoDES rats. The neonatal estrogenization affects negatively in several urodynamical parameters. Intraluminal pressure high-frequency oscillations (IPHFO) of bladder pressure are characteristic in male rat voiding. The first parameter is the bladder pressure (maximum- and mean pressures). The maximal and mean bladder pressures are calculated from the pressure oscillations. Maximal value is measured from the highest peak and the mean value from all oscillations. Both the maximal and mean bladder pressures were significantly higher in placebo treated neoDES rats (PD) than in placebo treated control rats (PC). Aromatase inhibitor treatment decreased significantly the maximum and mean bladder pressures of neoDES (AD) rats during voiding while no effect was seen in aromatase-inhibitor treated control (AC) animals (Table 1).

TABLE 1

Maximum and mean pressures (mmHg) of the bladder

|  | Mean | sd ± | n | p |
|---|---|---|---|---|
| Maximum |  |  |  |  |
| PC | 38.12 | 4.66 | 11 |  |
| AC | 39.15 | 2.11 | 11 | 0.5789 |
| PD | 45.35 | 6.13 | 11 | 0.0003 |
| AD | 42.21 | 3.38 | 12 | 0.0282 |
| Mean |  |  |  |  |
| PC | 28.02 | 3.25 | 11 |  |
| AC | 30.10 | 1.60 | 11 | 0.1197 |
| PD | 34.80 | 4.11 | 11 | >0.0001 |
| AD | 31.51 | 2.78 | 12 | 0.0093 |

The second parameter is the flow rate. The maximal and mean flow rates were significantly lower in PD rats compared to PC group. Aromatase inhibitor treatment increased significantly the maximum and mean flow rates of AD animals (Table 2).

TABLE 2

Maximum and mean flow rates (ml/min)

|  | Mean | sd ± | n | p |
|---|---|---|---|---|
| Maximum |  |  |  |  |
| PC | 29.80 | 11.84 | 11 |  |
| AC | 31.14 | 17.28 | 11 | 0.7986 |
| PD | 20.03 | 7.04 | 11 | 0.0339 |
| AD | 30.79 | 10.88 | 12 | 0.8067 |
| Mean |  |  |  |  |
| PC | 4.79 | 1.87 | 11 |  |
| AC | 6.54 | 4.22 | 11 | 0.1081 |
| PD | 2.63 | 1.04 | 11 | 0.0498 |
| AD | 5.02 | 1.74 | 12 | 0.8276 |

Figure 4A:
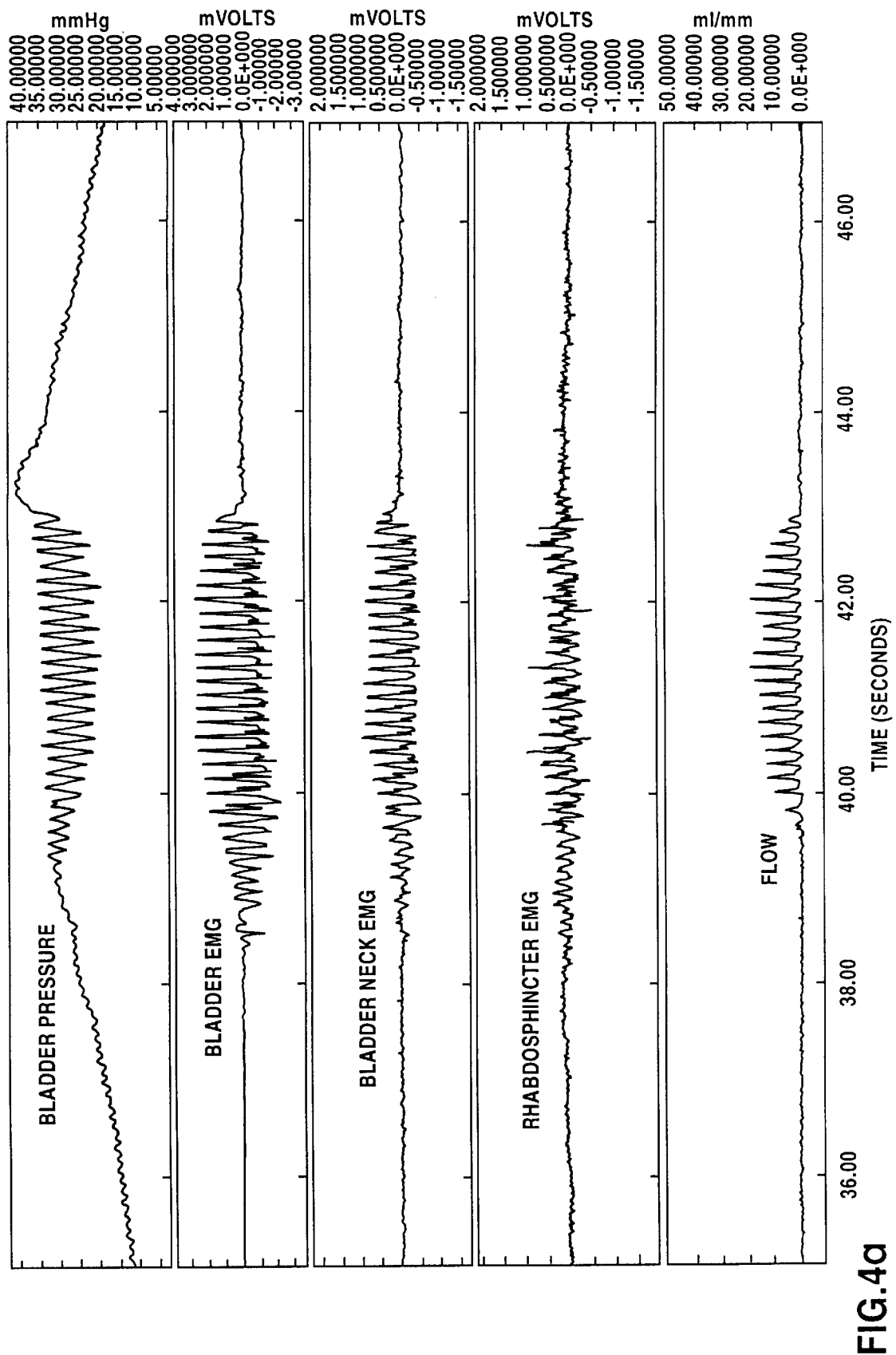
FIG. 4a shows the bladder pressure (in mmHg), electrical activity of the bladder neck (EMG), rhabdosphincter (EMG) and bladder (detrusor) (EMG) (electrical activity values in mVolt) and urine flow (in ml/min) versus time in a control rat as measured by the method according to this invention.
Figure 4B:
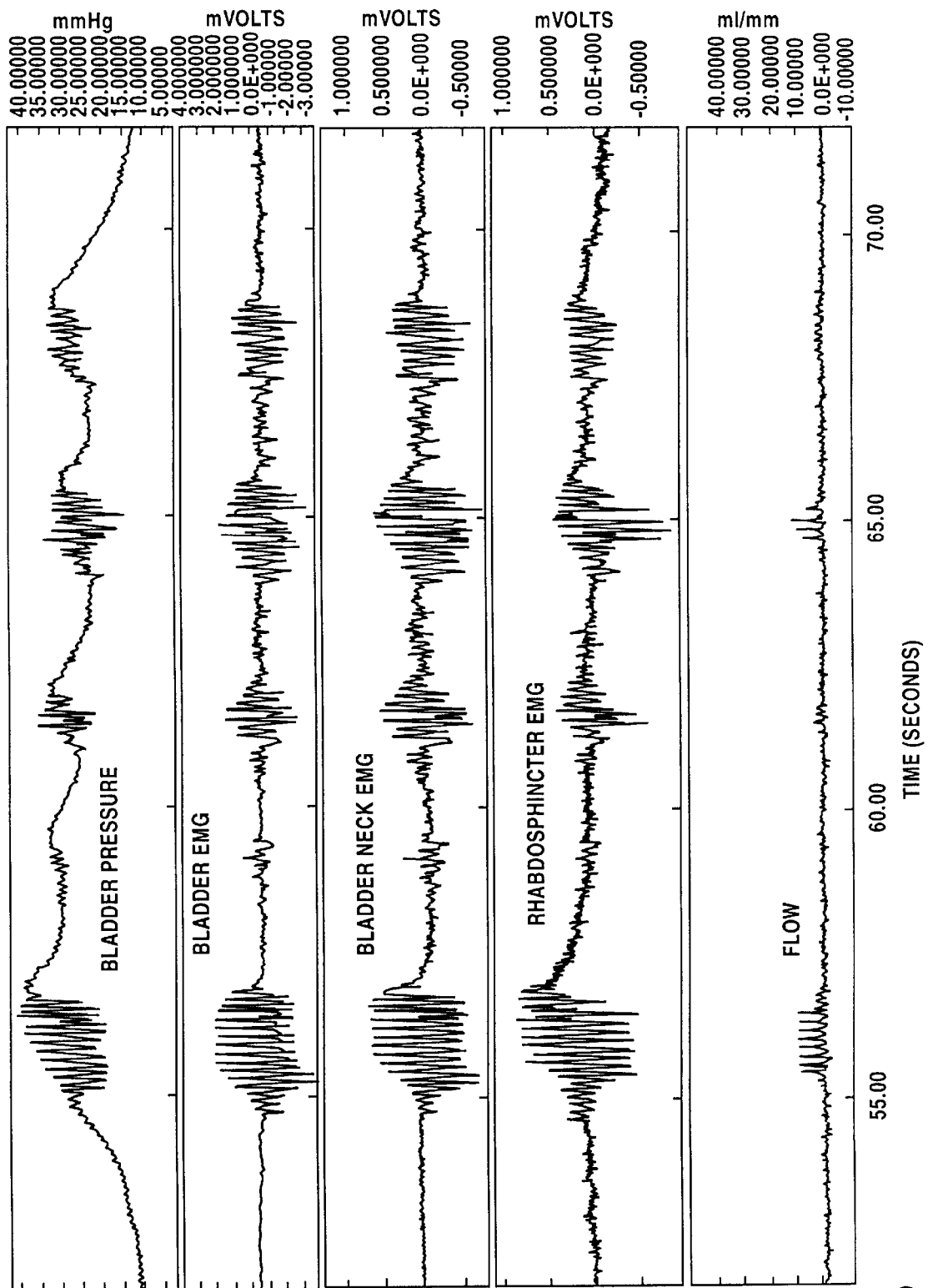
FIG. 4b shows the bladder pressure (in mmHg), electrical activity of the bladder neck, rhabdosphincter, bladder (detrusor) (electrical activity values in mVolt) and urine flow (in ml/min) versus time in a neoDES rat (neoDES rat= neonatally diethylstilbestrol (DES) treated rat) as measured by the method according to this invention.

The parameter of mean flow rate was chosen because of the micturition of the neoDES rats consists usually of several voidings (FIG. 4a represents one micturition of the control rat; FIG. 4b one micturition of the neoDES rat). This phenomena affects the duration of voiding of the neoDES rats, which is our third parameter. As mentioned the micturition time is lengthened significantly in PD animals. As can be seen from FIGS. 4a and 4b, in neoDES rats the urination takes place in several short fragments and micturition totally lasts longer than in control rats. In AD rats the time of urination has normalized. Even in AC group the micturition time is shorter than in PC group (Table 3).

TABLE 3

Micturition time (seconds)

|  | Mean | sd ± | n | p |
|---|---|---|---|---|
| PC | 7.10 | 2.75 | 11 |  |
| AC | 4.91 | 2.25 | 11 | 0.1421 |

TABLE 3-continued

Micturition time (seconds)

|  | Mean | sd ± | n | p |
|---|---|---|---|---|
| PD | 11.12 | 5.74 | 11 | 0.0210 |
| AD | 8.24 | 4.04 | 12 | 0.4315 |

Figure 5:
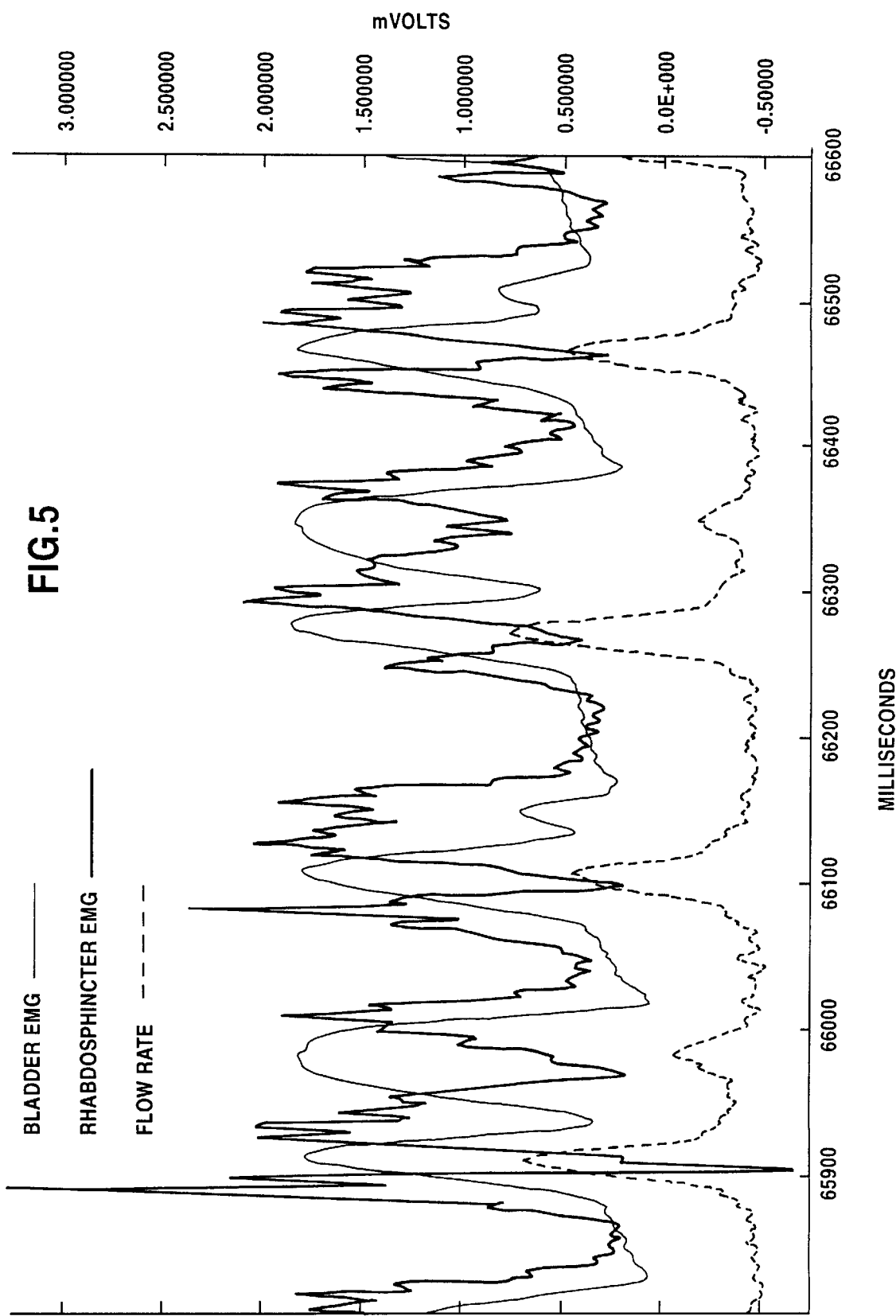
FIG. 5 shows the electrical activity of the striated urethral sphincter (rhabdosphincter; EMG), bladder (detrusor) (EMG) and urine flow rate versus time in a control rat.

The extracellular electrical activity of the detrusor, proximal urethra (bladder neck) and striated urethral sphincter was measured with flexible suction electrodes simultaneously with transvesical cystometry and flow rate, in order to analyse the role of bladder and urethral smooth muscles and the striated sphincter muscle (rhabdosphincter) in micturition. There was a good correspondence between voltage and pressure. High amplitude electrical activity starts in all three electrodes, when the IPHFO of pressure starts. The shape of electrical activity of the striated urethral sphincter muscle differs from that of the bladder smooth muscle. It's electrical activity simultaneously with the activity of the detrusor and and striated urethral sphincter indicates the closure of the urethra. In the early part of the oscillation, the AP's (AP=action potential) of the striated urethral sphincter appear to be in different phase compared to the AP's of the detrusor. When the flow peaks appear, the AP's have the same timing. When the first flow spikes appear the shape of AP's of the and striated urethral sphincter starts to differ from that of the detrusor. The AP's of the detrusor and striated urethral sphincter are simultaneous. It is impossible on hydrodynamical ground since the simultaneous activation should close the lumen of the and striated urethral sphincter and prevent the flow. The explanation for the controversy is a fast hyperpolarization in the middle of the AP of the and striated urethral sphincter (FIG. 5, arrow). The AP starts with a depolarization, but is overcome by the rapid hyperpolarization and it ends to the depolarization (FIG. 5). The timing of the hyperpolarization fits with the timing of the flow peaks (FIG. 5). The urethra seems to be open during the shortlasting hyperpolarizations. This cannot be seen in electrical activity of PD rats which show a single action potential (like in detrusor) (FIG. 6, arrow). This suggests a failure in the opening mechanisms of the striated urethral sphincter. Aromatase-inhibitor normalizes this detrusor urethral dyssynergia (FIG. 7, arrow) in AD group. The voiding is still possible in PD group even if there is this muscular failure in the striated urethral sphincter. This may be due to lengthened duration of the AP's of both detrusor and proximal urethra smooth muscles in PD rats in comparison with PC animals. The increase of the duration of the AP's is associated with hypertrophy of the detrusor and bladder neck muscles. This suggests that the strength of the detrusor has increased and it can force the urine trough the closed urethra. In AD group the duration of the smooth muscle AP's are decreased (Tables 4 and 5).

TABLE 4

Duration of the AP's in the detrusor in the beginning, in the middle and in the end of the IPHFO

| Duration (ms) | Mean | sd ± | n | p |
|---|---|---|---|---|
| beginning |  |  |  |  |
| PC | 0.105 | 0.005 | 8 |  |
| AC | 0.096 | 0.01 | 5 | 0.3619 |
| PD | 0.125 | 0.037 | 5 | 0.0590 |

TABLE 4-continued

Duration of the AP's in the detrusor in the
beginning, in the middle and in the end of the IPHFO

| Duration (ms) | Mean | sd ± | n | p |
|---|---|---|---|---|
| AD | 0.103 | 0.011 | 6 | 0.7897 |
| Middle | | | | |
| PC | 0.093 | 0.012 | 8 | |
| AC | 0.078 | 0.014 | 5 | 0.1018 |
| PD | 0.118 | 0.014 | 5 | 0.0058 |
| AD | 0.93 | 0.013 | 6 | 0.9568 |
| End | | | | |
| PC | 0.099 | 0.009 | 8 | |
| AC | 0.087 | 0.012 | 5 | 0.2458 |
| PD | 0.130 | 0.03 | 5 | 0.0059 |
| AD | 0.113 | 0.016 | 6 | 0.1764 |

TABLE 5

Duration of the AP's in the bladder neck in the
beginning, in the middle and in the end of the IPHFO

| Duration (ms) | Mean | sd ± | n | p |
|---|---|---|---|---|
| beginning | | | | |
| PC | 0.116 | 0.007 | 8 | |
| AC | 0.104 | 0.014 | 5 | 0.0997 |
| PD | 0.110 | 0.012 | 5 | 0.4152 |
| AD | 0.09 | 0.015 | 6 | 0.3374 |
| Middle | | | | |
| PC | 0.101 | 0.009 | 8 | |
| AC | 0.09 | 0.014 | 5 | 0.1554 |
| PD | 0.134 | 0.019 | 5 | 0.0003 |
| AD | 0.105 | 0.010 | 6 | 0.6338 |
| End | | | | |
| PC | 0.107 | 0.007 | 8 | |
| AC | 0.099 | 0.016 | 5 | 0.3772 |
| PD | 0.131 | 0.021 | 5 | 0.0161 |
| AD | 0.119 | 0.014 | 6 | 0.1726 |

The last of the parameters shows the amount of the residual urine. This is measured as follows. First the bladder is emptied with suction. During this time there is no infusion of saline in to the bladder. After emptying the bladder, the infusion (0,185 ml/min) is started. After the micturition (caused by infusion of the saline) the voided volume is collected in tubes. This volume is subtracted from the infused volume. Aromatase-inhibitor treatment does not affect the amount of residual urine in control rats. As can be seen in neoDES rats the amount of residual urine is increased significantly. The aromatase-inhibitor treatment (already in four weeks) reduces the residual urine. The values are shown in Table 6.

TABLE 6

Residual urine in milliliters (four week study)

| | Mean | sd ± | n | p |
|---|---|---|---|---|
| PC | 0.375 | 0.14 | 11 | |
| AC | 0.359 | 0.12 | 9 | 0.8522 |
| PD | 0.717 | 0.27 | 9 | 0.0003 |
| AD | 0.589 | 0.20 | 9 | 0.0152 |

The experiments show that MPV-2213ad treatment can reverse many of the detrimental effects of neoDES treatment. The beneficial effects of MPV-2213ad were seen in several parameters. In the four week study the results show beneficial effects, but they seldom reach a statistical significance. In the six week study the MPV-2213 ad normalizes the voiding dysfunction better. The results indicate that by increasing the length of the treatment it is possible to further increase the beneficial effect of the treatment.

Effect of an aromatase inhibitor on the concentrations of estradiol and testosterone in men In order to support the pharmacological effect of MPV-2213 ad in men, the said compound was given as a single dose of 0.03, 0.3, 3, 9, 30, 100, 300 and 600 mg. Number of test subjects/ dose level was 3 except for the doses of 300 and 600 mg were the number was 10 and 8, respectively. The study was a phase I study and it was conducted according to the Good Clinical Practise regulations. The concentrations of estradiol and testosterone were measured by Spectria RIA, Orion Diagnostica, Turku, Finland. Several other analyses were done but have not been described in this application. There were, however, no abnormalities to be found in the measured variables. As shown in table 7, the concentrations of estradiol fall significantly and the concentrations of testosterone increase slightly, but consistently as a function of dose. Higher doses have a longer duration of action than the lower ones. Increase of testosterone was most clear at higher doses and after 2–4 days after the single dose. The ratio androgen to estrogen increases significantly (several fold at high doses). These results show that the aromatase inhibitor MPV-2213ad has expected pharmacological property in men. The described study was a single dose study and it is understood that the effects are seen even more clearly during long-term administration of the inhibitor.

Similar types of results have been described with other aromatase inhibitors in clinical phase I studies (Vanden Bossche et al, 1994; Trunet et al, 1993) indicating that the rationale of this invention is valid also for other specific aromatase inhibitors. Such inhibitors include anastrozole, fadrozole, letrozole, vorozole (and enantiomers thereof), roglethimide, atamestane, exemestane, formestane, YM-511, ZD-1033, and NKS-01 (Drugs of the Future, 19:335–337, 1994).

TABLE 7

Test subjects' demographic data in the single dose
study of MPV-2213ad. Mean (SD) is presented.

| Dose (mg) | age (yrs) | height (cm) | weight (kg) |
|---|---|---|---|
| 0.03 | 23 (1.0) | 177 (10.6) | 69 (3.8) |
| 0.3 | 24 (0.6) | 181 (6.7) | 73 (1.2) |
| 3 | 22 (1.0) | 180 (9.1) | 81 (2.9) |
| 9 | 21 (1.2) | 177 (4.5) | 69 (7.5) |
| 30 | 20 (1.2) | 181 (5.3) | 78 (4.7) |
| 100 | 24 (4.7) | 176 (5.0) | 71 (5.0) |
| 300 | 24 (2.9) | 180 (6.0) | 73 (4.0) |
| 600 | 25 (3.1) | 180 (6.7) | 75 (8.7) |

TABLE 8

Estradiol and testosterone concentrations (mean (SD)) before and 1 and 2 days after single doses of MPV-2213ad as well as the ratio testosterone to estradiol. Mean (SD) is presented. T = testosterone, E = estradiol. The ratio T to E is calculated as T nmol/l/E pmol/l. Day 0 is the pretreatment value at 8 a.m. On days 1 and 2 the hormone concentrations were measured at the same time (at 8 a.m.) to eliminate the diurnal changes of the hormone concentrations.

| Dose (mg) | estradiol pmol/l (day 0) | estradiol pmol/l (day 1) | estradiol pmol/l (day 2) | testosterone nmol/l (day 0) | testosterone nmol/l (day 1) | testosterone nmol/l (day 2) |
|---|---|---|---|---|---|---|
| 0.03 | 124 (58.2) | 133 (63.9) | 124 (67.1) | 25 (4.2) | 25 (8.1) | 25 (6.9) |
| 0.3 | 97 (20.4) | 85 (15.5) | 95 (38.7) | 17 (4.6) | 19 (7.1) | 21 (9.1) |
| 3 | 92 (11.2) | 39 (5.5) | 89 (10.1) | 16 (3.5) | 16 (2.1) | 20 (5.0) |
| 9 | 155 (16.1) | 69 (2.5) | 149 (23.1) | 25 (3.0) | 29 (2.6) | 32 (5.9) |
| 30 | 159 (52.6) | 58 (19.9) | 130 (38.6) | 23 (1.2) | 31 (1.5) | 27 (3.1) |
| 100 | 116 (31.8) | 36 (13.4) | 58 (12.1) | 14 (5.5) | 17 (7.0) | 21 (6.0) |
| 300 | 115 (30.0) | 33 (12.8) | 55 (17.8) | 17 (3.3) | 24 (4.3) | 24 (4.1) |
| 600 | 101 (43.6) | 33 (16.6) | 51 (28.6) | 18 (5.1) | 23 (6.6) | 24 (8.7) |

| Dose (mg) | Ratio T to E (day 0) | Ratio T to E (day 1) | Ratio T to E (day 2) |
|---|---|---|---|
| 0.03 | 0.20 | 0.18 | 0.20 |
| 0.3 | 0.18 | 0.22 | 0.22 |
| 3 | 0.17 | 0.41 | 0.22 |
| 9 | 0.18 | 0.42 | 0.22 |
| 30 | 0.14 | 0.53 | 0.20 |
| 100 | 0.12 | 0.47 | 0.36 |
| 300 | 0.14 | 0.72 | 0.43 |
| 600 | 0.17 | 0.70 | 0.47 |

On the basis of the results obtained in the animal mode as described above for the study of detrusor urethral sphincter dyssynergia, we suggest that estrogens play an essential role in the development of the muscular dysfunction involved in detrusor urethral sphincter dyssynergia. Experiments in developmentally estrogenized rats with the aromatase inhibitor MPV-2213ad show that the estrogen-related neuromuscular changes are at least partially reversible. Experiments in young men (<40 yrs) show that with a single dose of MPV-2213ad estradiol concentrations fall dramatically and testosterone concentrations increase slightly enabling thus improvement of DATER.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

REFERENCES

Hinman, F. and Baumann, F. W. Vesical and ureteral damage from voiding dysfunction in boys without neurologic or obstructive disease. J. Urol. 109:727, 1973.

Hoffman, B. F., P. F. Cranefield, E. Lepeschkin, B. Surawick, and H. C. Herrlich. Comparison of cardiac monphasic action potentials recorded by intracellular and suction electrodes. Am. J. Physiol. 196(6):1297–1301, 1959.

Iosif, C. S., Batra, S., Ek.A. and Åstedt. Estrogen receptors in the human female lower urinary tract. Am. Obstet. Gynecol. 141:817, 1981.

Kaplan, S. A., Santarosa, R. P., d'Alisera, P. M., Fay, B. J., Ikeguchi, E. F., Hendrics, J. Klein, L. and Te, A. E. Pseudodyssynergia (contraction of the external phincter during voiding) misdiagnosed as chronic nonbacterila prostatitis and the role of biofeedback as a therapeutuc option. J. of Urol. 157:2234–2237, 1997.

Kaplan, S. A., Ikeguchi, E. F., Santarosa, R. P., d'Alisera, P. M., Hendrics, J. Klein, L., Te, A. E. and Miller, M. Etiology of voiding dysfunction in men less than 50 years of age. Urology 47:836–839, 1996.

Larsson, B., Andersson, K-E., Batra, S., Mattiasson, A. and Sjogren, C. Effects of Estradiol on Norepinephrine-Induced Contraction, Alpha Adrenoceptor Number and Norepinephrine Content in the Female Rabbit Urethra. The Journal of Pharmacology and Experimental Therapeutics 229:557–563, 1984.

Letrozole CGS-20267. Aromatase inhibitor. Drugs of the Future 19:335–337, 1994.

Maggi, C. A., P. Santicioli, and A. Meli. The nonstop transvesical cystometrogram in urethane-anesthetized rats. J. of Pharm. Meth. 15: 157–167, 1986a.

Morita, T., Tsuchiya, N., Tsuji, T. and Kondo, S. Changes of Autonomic Receptors Following Castration and Estrogen Administeration in the Male Rabbit Urethral Smooth Muscle. Tohoku J. Exp. Med. 166:403–405, 1992.

Oelrich, T. H. The Urethral Sphincter Muscle in the Male. Am. J. of Anat. 158:229–246, 1980.

Prostatic Obstruction. Pathogenesis and treatment. Ed. Christopher R. Chapple. Springer-Verlag 1994.

Rudy, D. C., Awad, S. A. and Downe, J. W. External sphincter dyssynergia: An abnormal continence reflex. J. of. Urol. 140:105–110, 1988.

Smith, P., Heimer, G., Norgren. and Ulmsten, U. Steroid Hormone Receptors in Pelvic Muscles and Ligaments in Women. Gynecol. Obstet. Invest. 30:27–30, 1990.

Strasser, H., Klima, G., Poisel, S., Horninger, W. and Bartsch, G. Anatomy and Innervation of the Rhabdosphincter of the Male Urethra. Prostate 28:24–31, 1996.

Trunet PF, Mueller Ph, Bhatnagar AS, Dickers I, Monnet G, White G: Open dose-finding study of a new potent and selective nonsteroidal aromatase inhibitor, CGS 20 267, in healthy male subjects. J Clin Endocrinol Metab 77: 319–323, 1993.

van Asselt, E., J. Groen, and R. van Mastrigt. A comparative study of voiding in rat and guinea pig: simultaneous measurement of flow rate and pressure. Am. J. of Physiol. 269 (Regulatory Integrative Comp. Physiol. 38): R98-R103, 1995.

Vanden Bossche H, Moereels H, Koymans LMH: Aromatae inhibitors—mechanism for non-steroidal inhibitors. Breast Cancer Res Treatm 30: 43–55, 1994

Wilson, P. D., Barker, G., Barnard, R. J. and Siddle, N. C. Steroid Hormone Receptors in the Female Urinary Tract. Urol. Int. 39:5–8, 1984.

Yabionsky, F., Savasta, M., Manier, M., Poirer, M., Lacolle, J. Y. and Freuerstein, C. Autoradiographic Localization of $\alpha_1$-Adrenoceptors in the Dog Prostate and Urehra With $^3$H-Prazosin. Neurourology and Urodynamics 10:257–266, 1991.

We claim:

1. A method for the treatment of (i) detrusor urethral sphincter dyssynergia in men, wherein said detrusor urethral sphincter dyssynergia is urethral dysfunction which is due to decreased androgen to estrogen ratio in a patient, or (ii) decreased androgen to estrogen ratio in men, said method comprising administering to the patient an effective amount of an aromatase inhibitor.

2. The method according to claim 1 wherein the aromatase inhibitor is a compound of selected from the group consisting of anastrozole, fadrozole, letrozole, vorozole, roglethimide, atamestane, exemestane, formestane, YM-511 (4-[N-(4-bromobenzyl)-N-(4-cyanophenyl)amino]-4H-1,2,4-triazole), ZD-1033 (arimedex) and NKS-01 (14-α-hydroxyandrost-4-ene-3,6,17-trione); or a compound of formula (I)

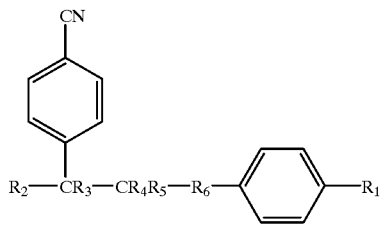

(I)

wherein $R_1$ is hydrogen, methyl, methoxy, nitro, amino, cyano, trifluoromethyl, difluoromethyl, monofluoromethyl or halogen; $R_2$ is a heterocyclic radical selected from 1-imidazolyl, triazolyl, tetrazolyl, pyrazolyl, pyrimidinyl, oxazolyl, thiazolyl, isoxazolyl and isothiazolyl; $R_3$ is hydrogen or hydroxy; $R_4$ is hydrogen; $R_5$ is hydrogen or hydroxy; or $R_4$ is hydrogen and $R_3$ and $R_5$ combined form a bond; or $R_3$ is hydrogen and $R_4$ and $R_5$ combined form =O; $R_6$ is methylene, ethylene, —CHOH—, —CH$_2$CHOH—, —CHOH—CH$_2$—, —CH=CH— or —C(=O)—; or $R_4$ is hydrogen and $R_3$ and $R_6$ combined is =CH— or =CH—CH$_2$—; or a stereoisomer, or a non-toxic pharmaceutically acceptable acid addition salt thereof.

3. The method according to claim 2 wherein the aromatase inhibiting compound is 1-[1-(4-cyanophenyl)-3-(4-fluorophenyl)-2-hydroxypropyl]-1,2,4-triazole, a stereoisomer or a non-toxic pharmaceutically acceptable acid addition salt thereof.

4. The method according to claim 3 wherein the aromatase inhibiting compound is 1-[1-(4-cyanophenyl)-3-(4-fluorophenyl) -2-hydroxypropyl]-1,2,4-triazole, diasteroisomer a+d.

5. The method according to claim 1 wherein said detrusor urethral sphincter dyssynergia in combination with enlargement of the prostate.

6. The method according to claim 1 wherein said detrusor urethral sphincter dyssynergia is not combined enlargement of the prostate.

7. The method according to claim 1 wherein the decreased androgen to estrogen ratio is expressed as symptoms related to the andropause.

8. The method according to claim 7 wherein said symptoms are selected from the group consisting of infertility, obesity, erectile dysfunction, impotence and gynecomastia.

* * * * *